United States Patent [19]

Goodman et al.

[11] Patent Number: 5,998,624
[45] Date of Patent: Dec. 7, 1999

[54] HALOISOQUINOLINE CARBOXAMIDE

[75] Inventors: Mark M. Goodman, Dunwoody; Randolph E. Patterson, Atlanta; R. W. Alexander, Atlanta; David Chappell, Atlanta, all of Ga.

[73] Assignee: Emory University, Atlanta, Ga.

[21] Appl. No.: 09/074,056

[22] Filed: May 7, 1998

Related U.S. Application Data

[60] Provisional application No. 60/045,902, May 7, 1997.

[51] Int. Cl.⁶ .................................................. C07D 217/26
[52] U.S. Cl. ............................................................ 546/146
[58] Field of Search .............................................. 546/146

[56] References Cited

U.S. PATENT DOCUMENTS

| | | | |
|---|---|---|---|
| 4,499,094 | 2/1985 | Dubroeucq | 514/301 |
| 4,684,652 | 8/1987 | Dubroeucq | 514/254 |
| 5,026,711 | 6/1991 | Mendes | 514/300 |
| 5,206,382 | 4/1993 | Costa | 548/494 |
| 5,212,181 | 5/1993 | Frost | 514/312 |

FOREIGN PATENT DOCUMENTS

| | | |
|---|---|---|
| B1 0210-084 | 8/1989 | European Pat. Off. . |
| 2525595 | 10/1983 | France . |

OTHER PUBLICATIONS

Nakatsuka, I. et al., "Preparation of radioactive isoquinolinecarboxamide derivatives with affinity for peripheral benzodiazepine receptors"; *Database HCAPLUS on STN*, 1995:90943, Jun. 27, 1995, Jpn., Kokai Tokkyo koho, 17 pp. (Abstract).

Gildersleeve et al, Nuclear Medicine & Biology, vol. 23, pp. 23–28, 1996.

Chemical Abstracts, Sumitomo Chemical Co., vol. 123,No. 23, Abstract No. 313, 785y, p. 883, Dec. 4, 1995.

Pike, V.W. et al. "Radioligands for PET Studies of Central Benzodiazepine Receptors and PK (Peripheral Benzodiazepine) Binding Sites—Current Status" (1993) Nucl. Med. Biol. 2:503–525.

Charbonneau, P. et al., "Peripheral type benzodiazepine receptors in the living heart characterized by positron emission tomography" (1986) Circulation 73:476–483.

Hashimoto, K. et al. "Synthesis and evaluation of $^{11}$C–PK 11195 for in vivo study of peripheral–type benzodiazepine receptors using positron emission tomography" (1989) Ann. Nucl. Med. 3:63–71.

Pascali et al. "The radiosynthesis of [$^{18}$F]PK 14105 as an alternative radioligand for peripheral type enzodiazepine binding sites" (1990) Appl. Radiat. Isot. 41:477–482.

*Primary Examiner*—Zinna Northington Davis
*Attorney, Agent, or Firm*—Greenlee, Winner and Sullivan, PC

[57] ABSTRACT

Compounds of the invention have the general structure

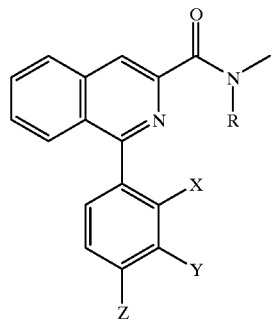

X, Y or Z are, respectively independently, H, F or an isotope thereof, Br or an isotope thereof, I or an isotope thereof, At or an isotope thereof, $(R_1)W$ or $(R_2)V$ and R is $—(R_1)W$, when W is H or F or an isotope thereof, $R_1$ is linear or branched alkyl of 1–4 carbon atoms, $R_2$ is vinyl, V is I or an isotope thereof and at least one of X, Y or Z is not H. The compounds of the invention bind to PK receptors.

18 Claims, No Drawings

HALOISOQUINOLINE CARBOXAMIDE

CROSS REFERENCE TO RELATED APPLICATIONS

Priority is claimed form U.S. Provisional Application Ser. No. 60/045,902, filed May 7, 1997.

STATEMENT RE FEDERALLY SPONSORED RESEARCH AND DEVELOPMENT

Not applicable

BACKGROUND OF THE INVENTION

The invention includes novel chemical compounds having specific binding in a biological system and capable of being used for positron emission tomography (PET) and single photon emission (SPECT) imaging methods.

The ability of analog compounds to bind to localized ligands within the body would make it possible, in principle, to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, [$^{11}$C], has been used for PET, but its short half-life of 20.5 minutes limits its usefulness to compounds that can be synthesized and purified quickly, and to facilities that are proximate to a cyclotron where the precursor [$^{11}$C] starting material is generated. Other isotopes have even shorter half-lives. [$^{13}$N] has a half-life of 10 minutes and [$^{15}$O] has an even shorter half-life of 2 minutes. The emissions of both are more energetic than those of [$^{11}$C]. Nevertheless, PET studies have been carried out with these isotopes (Hubner, K. F., in *Clinical Positron Emission Tomography*, Mosby Year Book, 1992, K. F. Hubner, et al., Chapter 2) A more useful isotope, [$^{18}$F], has a half-life of 110 minutes. This allows sufficient time for incorporation into a radio-labeled tracer, for purification and for administration into a human or animal subject. In addition, facilities more remote from a cyclotron, up to about a 200 mile radius, can make use of [$^{18}$F] labeled compounds. Disadvantages of [$^{18}$F] are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}$F-F. Reactions using $^{18}$F-F as starting material therefore yield products having only one half the radionuclide abundance of reactions utilizing K$^{18}$F as starting material. On the other hand, [$^{18}$F] can be prepared in curie quantities as fluoride ion for incorporation into a radiopharmaceutical compound in high specific activity, theoretically 1.7 Ci/nmol using carrier-free nucleophilic substitution reactions. The energy emission of [$^{18}$F] is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of [$^{18}$F] labeled compounds in PET has been limited to a few analog compounds. Most notably, [$^{18}$F]-fluorodeoxyglucose has been widely used in studies of glucose metabolism and localization of glucose uptake associated with brain activity. [$^{18}$F]-L-fluorodopa and other dopamine receptor analogs have also been used in mapping dopamine receptor distribution.

Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs. Astatine can be substituted for other halogen isotopes, [$^{210}$At] emits alpha particles with a half-life of 8.3 h. At-substituted compounds are therefore useful for tumor therapy, where binding is sufficiently tumor-specific.

Two classes of benzodiazapine receptors are known, having different locations and binding characteristics. In the central nervous system, particularly cerebral cortex, are the "BZ" receptors which are part of a complex that includes the GABA$_A$ receptor and a chloride ion channel and which functions in GABAA mediated neurotransmission. Classical benzodiazapines such as diazepain, act as agonists, having axiolytic, anti-convulsant, myorelaxant and amnesia-producing effects. Aumazenil is a specific BZ receptor binding compound which acts as an antagonist, having no direct effect but blocking the effects of agonists and inverse-agonists.

A second class of receptors (PK) are widespread throughout the human body, being especially prevalent on macrophages and glial cells. The PK receptors are found to be concentrated at sites of injury or inflammation. Specific tissue damage can be localized by observing a high concentration of PK receptors, in particular, at sites of brain injury, premorbid atherosclerotic plaque and neuronal injury in patients with intracranial tumor, multiple sclerosis and infarcts. The relative binding affinities of various benzodiazapines differ in BZ and PK receptors. Certain isoquinoline carboxamides have been shown to be potent and selective antagonists at the PK binding site. (Dubroeucq et al. French Patent No. 8,207,217. For a general review see Pike, V. W., et al. (1993) *Nucl. Med. Biol.* 2:503–525.) The compound PK11195 [1-(2-chlorophenyl)-N-methyl-N-(alkyl)-3-isoquinoline carboxamide] binds strongly to PK receptor sites.

PK receptor site distribution can be imaged using PET or SPECT, as shown by studies using [$^{11}$C]-labeled PK11195. [Charbonneau, P. et al. (1986) *Circulation* 73:476–483; Hashimoto, K. et al. (1989) *Ann. Nucl. Med.* 3:63–71. The potential clinical utility of PK11195 cannot be realized using ["C] label, as discussed.

A [$^{18}$F]-labeled analog, PK14105 has been described by Pascali et al. (1990) *Appl. Radiat. Isot.* 41:477–482, PK14105 is an analog of PK11195 with the C2 moiety replaced by [$^{18}$F] and a NO$_2$ group in sara orientation to the fluoro-group. The compound was labeled by nucleophilic substitution of the chloro analog by no-carrier-added (NCA) [$^{18}$F] produced in a cyclotron. However, the procedure required a tedious double pass through HPLC to remove the pharmacologically active chloro precursor. The purified product had a specific radioactivity of 0.4 Ci/Mmol. [For a general review of radioligands for both central and peripheral benzodiazapine receptors, see Pike, V. W., et al. (1993) Nucl. Med. Biol. 3:503–525].

Other substituted isoquinoline and quinoline carboxamides have been disclosed, some with halogen substituents. The compounds disclosed to date have been synthesized by processes that introduce the halogen at an early step in the process, which results in substantial loss of usable half-life because of the short half-lives of the nuclides most useful for PET and SPECT analysis. Notable examples include Dubroeucq, et al. U.S. Pat. No. 4,499,094 in which a halogen can exist as a substitutent of a phenyl group attached to the isoquinoline ring. European patent EPO B 0,210,084 describes substituted quinoline and isoquinoline carboxamides that can have halogen substituted on the non-heterocyclic ring, as well as on a phenyl attached to the heterocyclic ring. Synthesis was based on introducing the halogen at an early step or by using a halogenated starting material. Mendes, et al. U.S. Pat. No. 5,026,711 described quinoline carboxamide derivatives having the possibility of halogen substituted on the non-heterocyclic ring. Dubroeucq, et al. U.S. Pat. No. 4,684,652 described quinoline derivatives and isoquinolines (including carboxamides) having halogen substituted adjacent to the heterocyclic N or on the non-heterocyclic ring. The compounds were primarily specific for binding cerebral diazopine (BZ) receptors. Halogen substituted compounds were synthesized by a process that included introducing the halogen at an early stage of synthesis, by using a halogenated starting material. Costa, et al. U.S. Pat. No. 5,206,382 described substituted indoleacetamides having PK receptor binding activity. Halophenyl substituents were described. Synthesis was carried out by what may be deemed conventional early step halogen introduction. 1-oxo-quinoline derivatives having PK receptor binding activity have been described by Frost et al. U.S. Pat. No. 5,212,181.

SUMMARY OF THE INVENTION

Compounds of the invention have the general structure

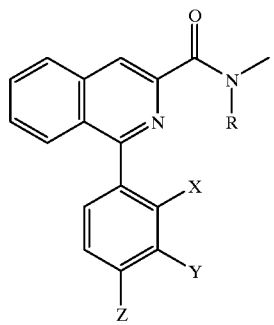

X, Y or Z are, respectively independently, H, F or an isotope thereof, Br or an isotope thereof, I or an isotope thereof, At or an isotope thereof, (R$_1$)W or (R$_2$)V and R is —(R$_1$)W, when W is H or F or an isotope thereof, R$_1$ is linear or branched alkyl of 1–4 carbon atoms, R$_2$ is vinyl, V is I or an isotope thereof and at least one of X, Y or is not H. The compounds of the invention bind to PK receptors. Where the halogen is a positron-emitting halogen isotope, the resulting compounds are useful for PET localization of PK receptors. Where the halogen is a γ-emitting halogen isotope, the resulting compounds are useful for SPECT localization of PK receptors. Compounds having two halogen substituents, such as X=I and R⁻ (CH$_2$)$_3$F, are preferred for analysis because the same chemical compound, appropriately labeled by a positron- or γ-emitting isotope, can be used for either PET or SPECT, making it possible to directly compare PET and SPECT results. Methods of synthesis have been developed to permit last step substitution of the halogen label such that the final compound was purified with high specific activity. As a result, the useable half-life of the isotope has been maximized. Useful halogens and isotopes thereof include F, $^{18}$F, Br, $^{75}$Br, $^{76}$Br, $^{77}$Br, $^{82}$Br, I, $^{123}$I, $^{124}$I, $^{125}$I, $^{131}$I, At, $^{211}$At and $^{210}$At. Compounds of the invention having stable isotopic substituents are useful for physiological therapy, behavioral therapy and studies thereof as can be understood from their PK receptor binding activity, and from the known activity of other PK receptor-binding compounds.

DETAILED DESCRIPTION OF THE INVENTION

Compounds of the invention have significant binding affinity for peripheral benzodiazapine (PK) receptors. The PK receptors are distributed throughout both the central nervous system and peripheral tissues, in particular on macrophage and glioma cells. Radiolabeled compounds of the invention are therefore useful for imaging the distribution of macrophage and/or glioma cells, either by PET or SPECT methods. Since macrophages concentrate at sites of ischemic injury, the compounds are useful for imaging is areas of ischemic injury such as occur in stroke, heart attack or bowel infarct. In addition, concentrations of glioma cells can be imaged, providing diagnosis of certain brain tumors. The compounds of the invention are synthesizable by steps which permit addition of the short-lived isotopic halogen at the last step, thereby providing greatly improved useable life time, increased useable geographic radius from the site of isotope generation, and improved image quality. Compounds of the invention having two halogen substituents, e.g. I and F, can be prepared either with isotopic iodine, e.g. $^{123}$I, for SPECT imaging, or with isotopic fluorine, e.g. $^{18}$F, for PET imaging, so that the respective PET and SPECT images can be directly compared for the same compound. The compounds are PK receptor antagonists, a physiological effect which has pharmacological and therapeutic utility.

The binding affinities of representative compounds of the invention are given in Table I. In this study, the compounds having the generic structure defined, supra, were tested for their ability to inhibit the binding of a known PK receptor antagonist [$^3$H]PK11195, to PK receptors in a rat kidney homogenate preparation.

Binding Assays

Tissue preparations of rat kidney homogenate were incubated with [$^3$H]PK11195 and competitors (i.e. 9a–d & 23a–c, at 12 concentrations ranging from 10$^{-11}$ to 10$^{-6}$nM) in an assay buffer. The assay mixture was incubated for 60 min. at room temperature with stirring and the resulting samples were rapidly filtered through Whatman GF/B glass-fiber filters pretreated with 0.2% protamine base and washed with cold buffer, pH 7.4. The filters were counted in a liquid scintillation counter at an efficiency of 65% for tritium saturation binding, Scatchard and competition experiments were analyzed with the iterative nonlinear least squares curve-fitting program. The results are shown in Table 1. For comparison, for PK11195, X is Cl, Y and Z are H, and R is 2-butyl. Compounds having the lower Ki values were the most As effective inhibitors, and therefore bound the PK-receptor at the lowest concentrations. Compounds of the invention are also useful for radiation therapy, based on their specific affinity for glial tumor cells. Preferred isotopes for therapeutic use include $^{131}$I, $^{124}$I, $^{211}$At and $^{210}$At.

TABLE 1

Inhibition of [$^3$H]PK11195 with [1-(iodophenyl)-N-methyl-N-(fluoroalkyl)-3-isoquinoline carboxamide] analogs

| Compound | | | | Ki (nM) (Average; N-2) |
|---|---|---|---|---|
| $X_1$ | $Y_1$ | $Z_1$ | R | Ki |
| -I | -H | -H | CH$_2$CH$_2$CH$_2$F | 0.26 |
| -H | -I | -H | CH$_2$CH$_2$CH$_2$F | 1.30 |
| -H | -H | -I | CH$_2$CH$_2$CH$_2$F | 63.10 |
| -I | -H | -H | CH$_2$CH$_2$F | 421 |
| -I | -H | -H | CH$_3$CHCH$_2$CH$_3$ | 0.25 |
| -H | -I | -H | CH$_3$CHCH$_2$CH$_3$ | 2.80 |
| -H | -H | -I | CH$_3$CHCH$_2$CH$_3$ | 3.10 |
| -I | -H | -H | CH$_3$CHCH$_2$CH$_3$ | 6.32 |
| -H | -I | -H | CH$_3$CHCH$_2$CH$_3$ | 1.53 |
| -H | -H | -I | CH$_3$CHCH$_2$CH$_3$ | 1.60 |

In particular the invention provides a method for conducting positron emission tomography of a subject comprising:

1) administering to the subject an image-generating amount of a compound of the invention which contains at least one of the following: $^{76}$Br, $^{75}$Br, $^{124}$I and $^{18}$F, and
2) measuring the distribution within the subject of the compound by positron emission tomography. Also provided is a method for conducting single photon emission imaging of a subject comprising:
1) administering to the subject an image-generating amount of a compound of Formula I which contains at least one of the following: $^{77}$Br, $^{82}$Br, $^{123}$I or $^{131}$I, and
2) measuring the distribution within the subject of the compound by single photon emission tomography.

Synthesis of compounds of the invention has been especially devised such that a halogen-moiety can be substituted for a leaving group as the last step of synthesis, in a rapid reaction which, if the halogen is a radio-isotope, provides the isotopically-labeled compound in high radiochemical yield. Such non-traditional synthesis is required because many of the most useful isotopes have such short half-lives that conventional synthetic means would be so time-consuming that the isotope would be significantly decayed, or lost. Schemes 1–6 diagram exemplary synthetic routes for the compounds of the invention. Further provided by their invention is a kit for the rapid synthesis of a compound of the invention. The kit includes a precursor compound of the invention, having a leaving group at the intended site of isotopic halogenation, such as, for example, compounds 14, 15 and 17. Optionally, the kit can include items of apparatus, such as a reaction vessel, device for transferring isotopic material to the reaction vessel, pre-packed separation column for separating unreached reactants from product, shielding, and the like, as known in the art. See, e.g. Zea-Ponce, Y., et al. (1998) *J. Nuclear Med.* 36:525–529.

Also included in the kit is a reagent capable of displacing the leaving group with a constituent containing an isotopic halogen. For example, as is known in the art, Na$^{124}$I can be oxidized to $^{124}$ICl. $^{124}$ICl can then be reacted with a precursor compound of the invention, as described, to yield a compound of the invention. The longer-lived isotopes, such as $^{123}$I with a half-life of 13 hours, are commercially available from sources such as Norion International Ltd. (Vancouver, B.C., Canada) or NEN/DuPont (N. Billerica, Mass.). Shorter-lived isotopes, such as $^{18}$F can be obtained from a regional source, within a ~200 mile radius of the site of intended use.

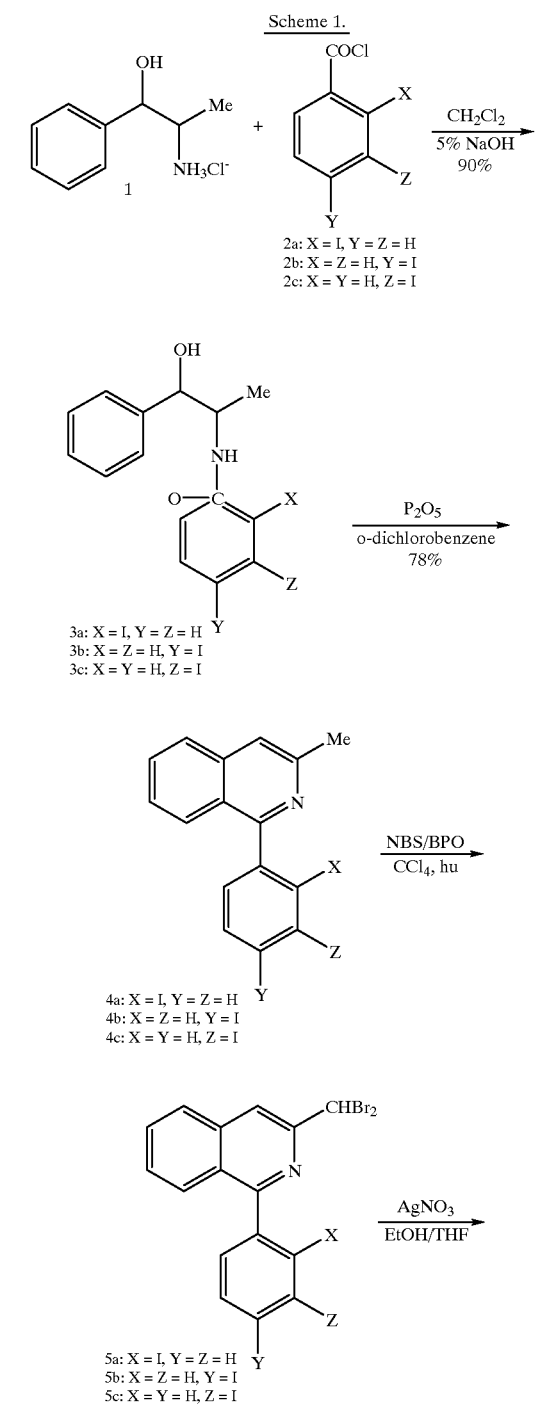

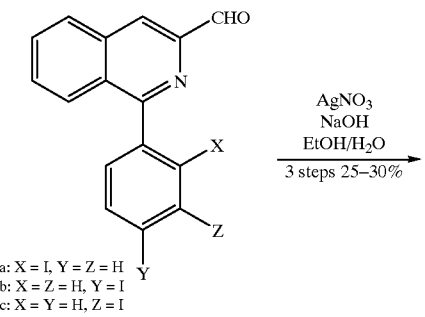
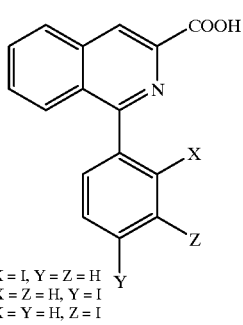
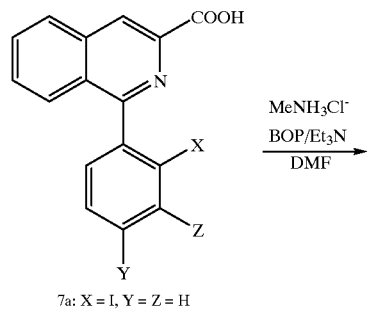
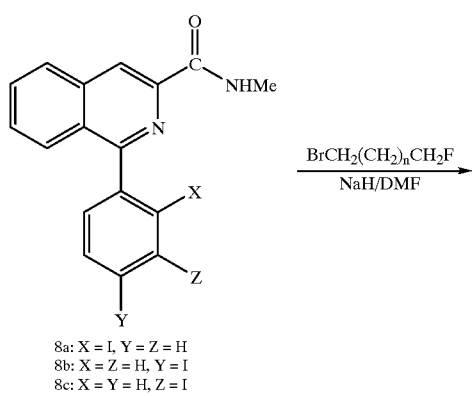
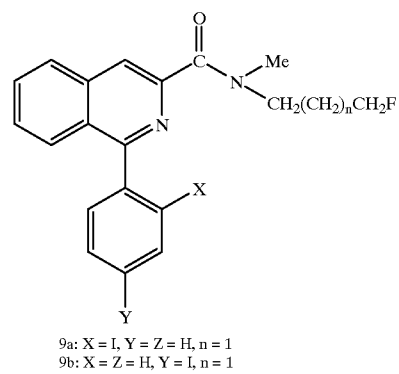
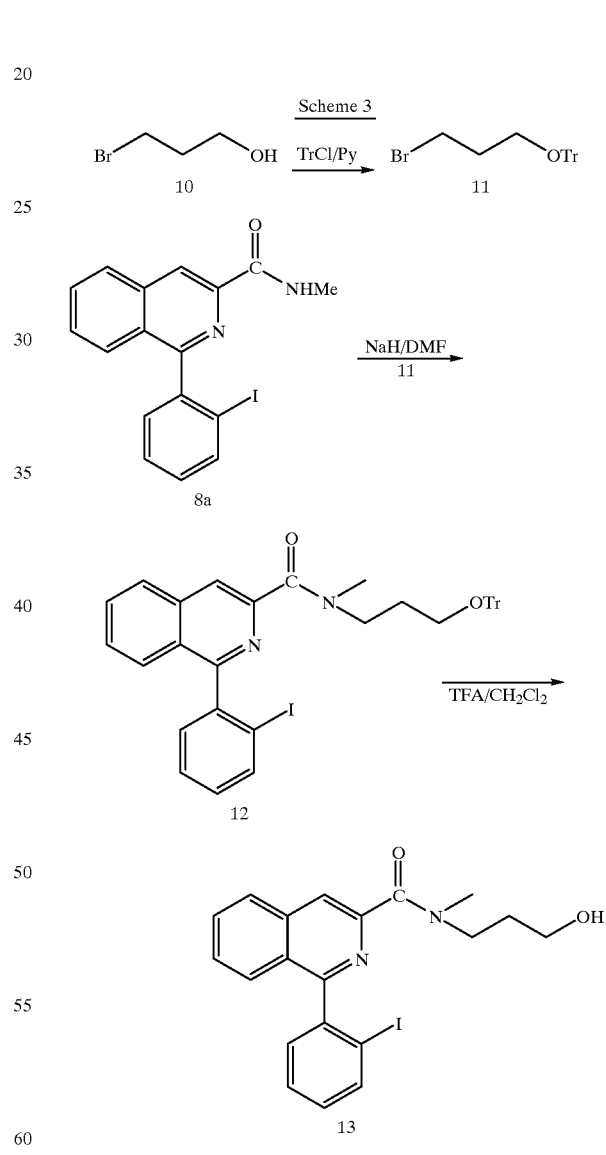

Scheme 4.
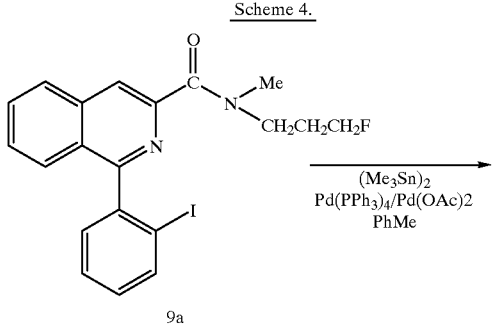
9a
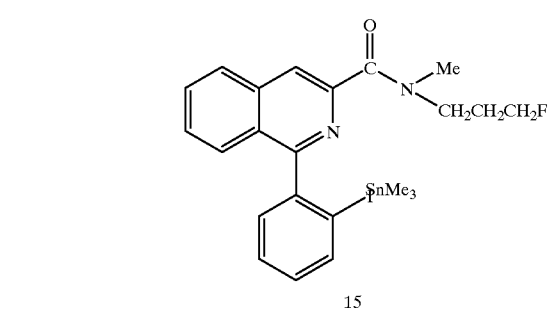
15
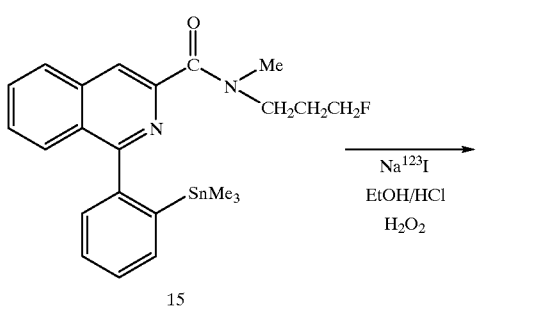
15
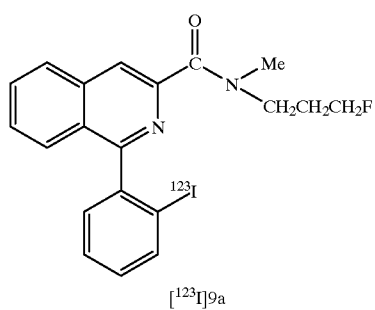
[$^{123}$I]9a
Scheme 5.
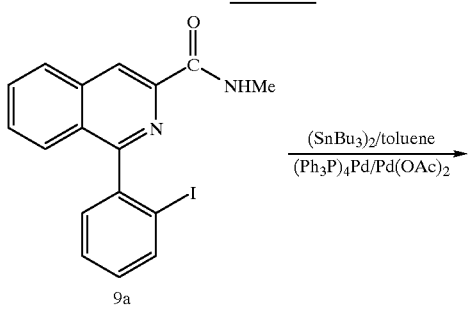
9a
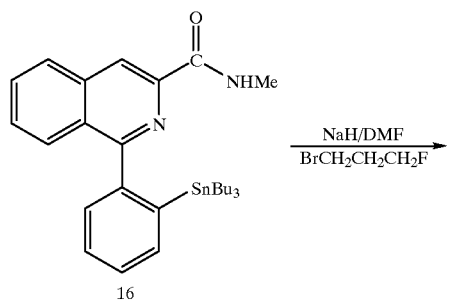
16
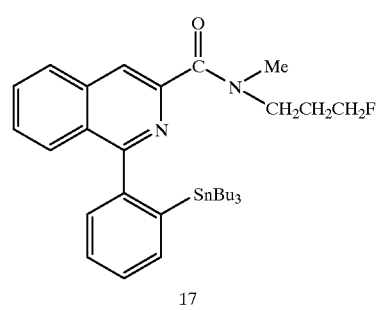
17
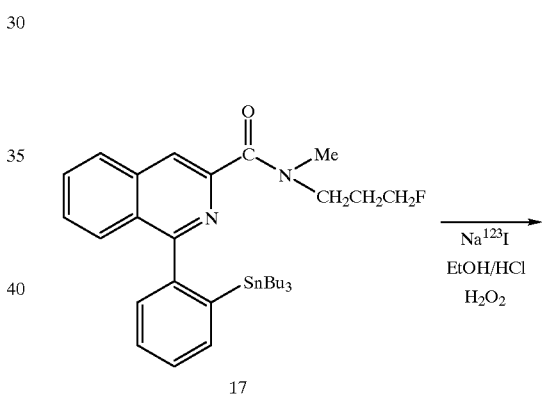
17
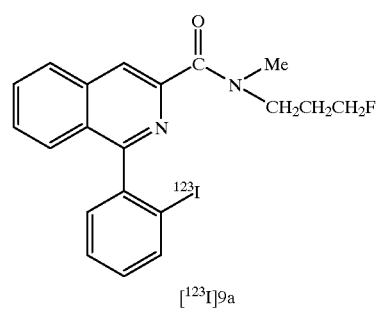
[$^{123}$I]9a

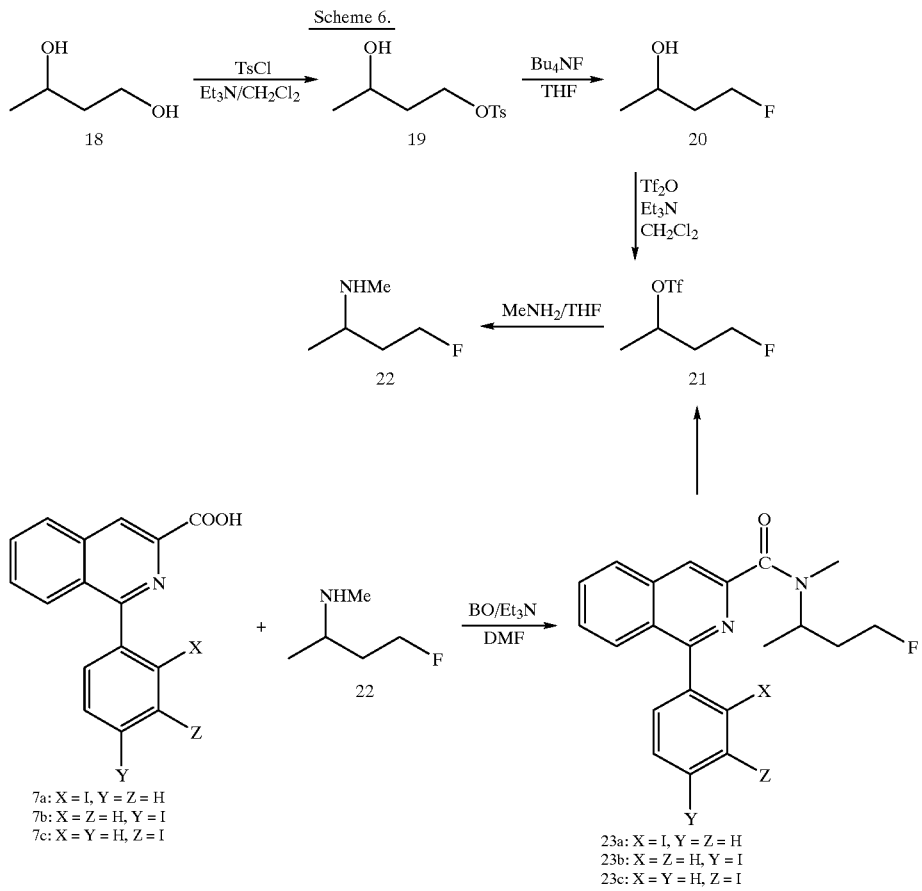

Scheme 6.

EXPERIMENTAL SECTION

The melting points were determined in capillary tubes using a Electrothermal-9100 melting point apparatus and uncorrected. The NMR spectra were obtained on GE-300 MHz spectrometers using tetramethylsilane as internal standard. The HRMS spectra was determined on VG-705 high resolution EI or JEOL JMS SX 102/SX102/E machines in the Mass Center at Emory University. The elemental analyses were performed by Atlantic Microlab, INC., Norcross, Ga. 30091.

It will be understood that compounds of the invention can be labeled with an isotope of any atom or combination of atoms in the structure. While [$^{18}$F] and [$^{123}$] have been emphasized herein as being particularly useful for PET and SPECT imaging, other uses are contemplated and will be apparent to those skilled in the art. For example, without limitation, compounds of the invention can be labeled with [$^{14}$C] to provide a tracer useful for biochemical studies of PK receptor. In addition, the binding studies reported herein demonstrate a pharmacological effect of compounds of the invention which can be utilized for physiological and behavioral studies and therapies, as will be apparent to those skilled in the art.

Example 1

2-iodo-N-(2-hydroxy-1-methyl-2-phenylethyl) benzamide (3a)

To a ice-cooled mixture of norephedrine hydrochloride (1) (5.2 g, 27.8 mmol) in CH$_2$Cl$_2$ (120 mL) and 5% NaOH aqueous solution (40 mL) was added dropwise a solution of 2-Iodobenzoyl chloride (2a, 7.5 g, 28.1 mmol) in CH$_2$CL$_2$ (15 mL). The resulting mixture was stirred at 0° C. for 4 h. The solvent was removed in vacuo. The residue was washed with H$_2$O, then dried, and recrystallized from EtOH to afford a white solid (9.5 g, 90%). mp 129–130° C. $^1$H NMR (CDCl$_3$) d 1.06 (d, J=6.9 Hz, 3 H, CH$_3$), 3.58 (bs, $^1$H, —CHCH$_3$), 4.95 (d, J=2.7 Hz, 1 H, —CHOH), 6.19 (d, J=8.4 Hz, 1 H, NH), 7.01–7.06 (m, 1 H, aromatic), 7.2–7.39 (m, 7 H, aromatic), 7.77 (d, J=7.8 Hz, 1 H, aromatic). $^{13}$C NMR (CDCl$_3$) d 13.74 (q, CH$_3$), 51.55 (d, —CHCH$_3$), 75.64 (d, —CHOH), 92.44 (s, =CI—, aromatic), 126.02 (d, aromatic), 126.13 (d, aromatic), 127.45 (d, aromatic), 128.07 (d, aromatic), 128.17 (d, aromatic), 139.70 (d, aromatic), 140.66 (s, aromatic), 141.85 (s, aromatic), 169.57 (s, —CONH—). Anal. Calcd. for C$_{16}$H$_{16}$INO$_2$: C, 50.41; H, 4.23; N, 3.67. Found: C, 50.25; H, 4.18; N, 3.58.

Example 2

3-iodo-N-(2-hydroxy-1-methyl-2-phenylethyl) benzamide (3b)

To a ice-cooled mixture of norephedrine hydrochloride (1) (7.02 g, 37.5 mmol) in Et$_2$O (165 mL) and 55 NaOH aqueous solution (60 mL) was added dropwise a solution of 3-Iodobenzoyl chloride (2b, 10 g, 37.5 mmol) in Et$_2$O (100 mL). After the addition had completed, the resulting mixture was stirred at 0° C. for 4 h. The solvent was removed in vacuo. The residue was washed with H$_2$O, dried, the recrystallized from EtOH to provide a white solid (12.84 g, 90%).

mp 139–140.5° C. $^1$H NMR (CDCl$_3$) d 1.10 (d, J=) 6.9 Hz, 3 H, CH$_3$), 3.51 (d, J=3.3 Hz, 1 H, —CHCH$_3$), 4.42–4.52 (m, 1 H, —OH), 4.97 (bs, 1 H, —CHOH), 6.42 (d, J=7.8 Hz, 1 H, NH), 7.14 (t, J=7.8 Hz, 1 H, aromatic), 7.25–7.42 (m, 5 H, aromatic), 7.69 (d, J=7.8 Hz, 1 H, aromatic), 7.82 (d, J=8.1 Hz, 1 H, aromatic), 8.08 (s, 1 H, aromatic). $^{13}$C NMR (CDCl$_3$) d 14.20 (q, CH$_3$), 51.45 (d, —CHCH$_3$), 76.18 (d, —CHOH), 94.24 (s, =CI—, aromatic), 126.14 (d, 2C, aromatic), 127.63 (d, aromatic), 128.26 (d, aromatic), 130.19 (d, aromatic), 136.00 (d, aromatic), 136.25 (s, aromatic), 140.41 (d, aromatic), 140.55 (s, aromatic), 166.26 (s, aromatic). Anal. Calcd. for C$_{16}$H$_{16}$INO$_2$: C, 50.41; H, 4.23; N, 3.67. Found: C, 50.48; H, 4.28; N, 3.62.

Example 3

4-iodo-N-(2-hydroxy-1-methyl-2-phenylethyl) benzamide (3c)

To a ice-cooled mixture of norephedrine hydrochloride (1) (7.02 g, 37.5 mmol) in CH$_2$Cl$_2$ (180 mL) and 5% NaOH aqueous solution (60 mL) was added dropwise a solution of 4-Iodobenzoyl chloride (2c, 10.1 g, 37.9 mmol) in CH$_2$Cl$_2$ (100 mL). After the addition had completed, the resulting mixture was stirred at 0° C. for 4 h. The solvent was removed in vacuo. The residue was washed with H$_2$O, dried, the recrystallized from EtOH to provide a white solid (12.8 g, 90%). mp 209–210° C. $^1$H NMR (DMSO-d$_6$) d 1.03 (d, J=6.6 Hz, 3 H, CH$_3$), 4.05–4.12 (m, 1 H, —CHCH$_3$), 4.65 (s, 1 H, —CHOH), 5.46 (d, J=3.6 Hz, 1 H, NH), 7.14 (t, J=7.2 Hz, 1 H, aromatic), 7.23 (t, J=7.5 Hz, 2 H, aromatic), 7.32 (d, J=7.2 Hz, 2 H, aromatic), 7.53 (d, J=8.4 Hz, 2 H, aromatic), 7.75 (d, J=8.1 Hz, 2 H, aromatic), 8.30 (d, J=8.4 Hz, 1 H, aromatic). $^{13}$C NMR (DMSO-d$_6$) d 14.70 (q, CH$_3$), 51.30 (d, —CHCH$_3$), 74.41 (d, —CHOH), 98.48 (s, =CI—, aromatic), 126.23 (d, aromatic), 126.73 (d, aromatic), 127.75 (d, aromatic), 129.29 (d, aromatic), 134.19 (s, aromatic), 137.03 (d, aromatic), 143.59 (s, aromatic), 164.70 (s, aromatic). Anal. Calcd. for C$_{16}$H$_{16}$INO$_2$: C, 50.41; H, 4.23; N, 3.67. Found: C, 50.35; H, 4.24; N, 3.65.

Example 4

1-(2-iodophenyl)-3-methylisoquinoline (4a)

A mixture of amide 3a, 9.5 g, 24.9 mmol) and P$_2$O$_5$ (44 g) in o-dichlorobenzene (150 mL) was refluxed for overnight. After it was cooled to room temperature, it was cooled to 0° C. by application of an external ice-water bath. To this cooled mixture was cautiously added 300 mL of H$_2$O. After the vigorous reaction had subsided, the dark solution was washed with toluene (2×50 mL). The aqueous layer was cooled to 0° C. and made to pH>11 with 50% aqueous NaOH. The resulting mixture was extracted with toluene (4×50 mL). The organic layers were dried (MgSO$_4$), filtered. The filtrate was concentrated in vacuo. The residue was recrystallized from benzene, thereby affording a white solid (6.68 g, 80%). mp 111–112° C. $^1$H NMR (CDCl$_3$) d 2.67 (s, 3 H, CH$_3$), 7.00–7.05 (m, 1 H, aromatic), 7.26–7.52 (m, 6 H, aromatic), 7.65 (d, J=8.1 Hz, 1 H, aromatic), 7.88 (d, J=8.1 Hz, 1 H, aromatic). $^{13}$C NMR (CDCl$_3$) d 24.05 (q, CH$_3$), 97.82 (s, =CI—, aromatic), 118.26 (d, aromatic), 124.45 (s, aromatic), 125.98 (d, aromatic), 126.77 (d, aromatic), 127.70 (d, aromatic), 129.43 (d, aromatic), 129.79 (d, aromatic), 129.92 (d, aromatic), 136.73 (s, aromatic), 138.78 (d, aromatic), 143.74 (s, aromatic), 150.24 (s, aromatic), 161.34 (s, =CCH$_3$—, aromatic). Anal. Calcd for C$_{16}$H$_{12}$IN: C, 55.67; H, 3.50; N, 4.06. Found: C, 55.77; H, 3.51; N, 3.96.

Example 5

1-(3-iodophenyl)-3-methylisoquinoline (4b)

A mixture of amide 3b, 11.54 g, 30.3 mmol) and P$_2$O$_5$ (43 g) in o-dichlorobenzene (150 mL) was refluxed for 20 h. After it was cooled to room temperature, it was cooled to 0° C. by application of an external ice-water bath. To this cooled mixture was cautiously added 300 mL of H$_2$O. After the vigorous reaction had subsided, the dark solution was washed with toluene (2×50 mL). The aqueous layer was cooled to 0° C. and made to pH >11 with 50% aqueous NaOH. The resulting mixture was extracted with toluene (4×50 mL). The organic layers were dried (MgSO$_4$), filtered. The filtrate was concentrated in vacuo. The residue was recrystallized from benzene, thereby affording a white solid (6.5 g, 62%) mp 77–78° C. $^1$H NMR (CDCl$_3$) d 2.72 (s, 3 H, CH$_3$), 7.23 (t, J=7.8 Hz, 1 H, aromatic), 7.40–7.52 (m, 2 H, aromatic), 7.57–7.66 (m, 2 H, aromatic), 7.71–7.85 (m, 2 H, aromatic), 7.92 (d, J=8.7 Hz, 1 H, aromatic), 8.02 (s, 1 H, aromatic). $^{13}$C NMR (CDCl$_3$) d 24.31 (q, CH$_3$), 94.31 (s, =CI—, aromatic), 118.36 (d, aromatic), 126.39 (d, 2C, aromatic), 126.92 (d, aromatic), 129.08 (d, aromatic), 129.83 (d, aromatic), 129.99 (d, aromatic), 137.34 (d, aromatic), 137.47 (s, aromatic), 138.53 (d, aromatic), 141.70 (s, aromatic), 150.80 (s, aromatic), 158.36 (s, =CCH$_3$—, aromatic). Anal. Calcd for C$_{16}$H$_{12}$IN: C, 55.67; H, 3.50; N, 4.06. Found: C, 55.53; H, 3.56; N, 4.05.

Example 6

1-(4-iodophenyl)-3-methylisoquinoline (4c)

A mixture of amide 3c, 8.54 g, 22.4 mmol) and P$_2$O$_5$ (40 g) in o-dichlorobenzene (140 mL) was refluxed for overnight, then cooled to room temperature. It was cooled to 0° C. by application of an external ice-water bath. To this cooled mixture was cautiously added 200 mL of H$_2$O. After the vigorous reaction had subsided, the dark solution was washed with toluene (2×40 mL). The aqueous layer was cooled to 0° C. and made to pH >11 with 50% aqueous NaOH. The resulting mixture was extracted with toluene (4×50 mL). The organic layers were dried (MgSO$_4$), filtered. The filtrate was concentrated in vacuo. The residue was recrystallized from benzene, thereby affording a white solid (6.1 g, 79%). mp 146.5–147.4° C. $^1$H NMR (CDCl$_3$) d 2.72 (s, 3 H, CH$_3$), 7.38–7.51 (m, 4 H, aromatic) 7.61 (t, J=6.9 Hz, 1 H, aromatic), 7.75 (d, J=8.1 Hz, 1 H, aromatic), 7.84 (d, J=8.1 Hz, 1 H, aromatic), 7.94 (d, J=8.7 Hz, 1 H, aromatic). $^{13}$C NMR (CDCl$_3$) d 24.34 (q, CH$_3$), 94.58 (s, =CI—, aromatic), 118.20 (d, aromatic), 124.56 (s, aromatic), 126.31 (d, aromatic), 126.42 (d, aromatic), 126.94 (d, aromatic), 129.96 (d, aromatic), 131.68 (d, aromatic), 137.41 (d, aromatic), 137.51 (s, aromatic), 139.12 (s, aromatic), 150.88 (s, aromatic), 158.97 (s, =CCH$_3$—, aromatic). Anal. Calcd for C$_{16}$H$_{12}$IN: C, 55.67; H, 3.50; N, 4.06. Found: C, 55.63; H, 3.55; N, 4.07.

Example 7

1-(2-iodophenyl)-3-isoquinolinecarboxylic Acid (7a)

A mixture of 1-(2-iodophenyl)-3-methylisoquinoline (6.86 g, 19.88 mmol), N-bromosuccinimide (NBS) (8.896 g, 49.98 mmol), and benzoyl peroxide (BPO) (0.57 g) in CCl$_4$ (100 mL) was heated to reflux while being illuminated by a flood lamp for 5 h. The reaction mixture was cooled to room temperature and filtered. The filtrate was washed with saturated NaHCO$_3$ aqueous solution (1×40 mL), dried (Na$_2$SO$_4$), then filtered. The filtrate was concentrated in vacuo, thereby affording crude 1-(2-iodophenyl)-3-dibromomethylisoquinoline (10.43 g) as a yellow oil. It was used directly in next step without any purifications. To a refluxing solution of crude dibromide (10.43 g) in EtOH (140 mL) and THF (70 mL) was added dropwise a solution of AgNO$_3$ (10.595 g) in H$_2$O (6 mL). The mixture was refluxed for 1 h and filtered while hot. The filter cake was washed with hot THF (2×20 mL). The combined filtrate was concentrated in vacuo to give crude 1-(2-Iodophenyl)-3-isoquinoline-carboxaldehyde as an dark yellow oil (9 g). This oil was used without further purification. To a solution of crude aldehyde (9.0 g) in absolute EtOH (100 mL) was slowly added a solution of AgNO$_3$ (11.11 g) in H$_2$O (10 mL). To this stirred solution was added dropwise a solution of NaOH (9.43 g) in H$_2$O (140 mL). The resulting black slurry was stirred at room temperature for 2 h. Then the mixture was filtered through a small Celite column. The filter cake was washed with ether. The ether was evaporated and the aqueous solution was made slightly acidic with concentrated HCl. The precipitate was collected by filtration, then washed with H$_2$O. It was recrystallized from CH$_3$CN, thereby affording a pale yellow crystalline (2.63 g, 35%). mp 174.4–175.8° C. $^1$H NMR (DMSO-d$_6$+D$_2$O) d 7.32 (t, J=7.5 Hz, 1 H, aromatic), 7.46 (d, J=8.1 Hz, 1 H, aromatic), 7.51 (d, J=8.4 Hz, 1 H, aromatic), 7.60 (t, J=7.2 Hz, 1 H, aromatic), 7.77 (t, J=7.8 Hz, 1 H, aromatic), 7.91 (t, J=7.5 Hz, 1 H, aromatic), 8.03 (d, J=8.1 Hz, 1 H, aromatic), 8.30 (d, J=8.1 Hz, 1 H, aromatic), 8.76 (s, 1 H, aromatic). HRMS Calcd for C$_{16}$H$_{10}$INO$_2$: 374.9756. Found: 374.9756.

Example 8

1-(3-iodophenyl)-3-isoquinolinecarboxylic Acid (7b)

A mixture of 1-(3-iodophenyl)-3-methylisoquinoline (5.733 g, 16.62 mmol), N-bromosuccinimide (NBS) (7.399 g, 41.57 mmol), and benzoyl peroxide (BPO) (0.48 g) in CCl$_4$ (100 mL) was heated to reflux while being illuminated by a flood lamp for 5 h. The reaction mixture was cooled to room temperature and filtered. The filtrate was washed with saturated NaHCO$_3$ aqueous solution (40 mL), dried (Na$_2$SO$_4$), then filtered. The filtrate was concentrated in vacuo, thereby affording crude 1-(3-iodophenyl)-3-dibromomethylisoquinoline (8.327 g) as a yellow oil. It was used directly in next step without any purifications. To a refluxing solution of crude dibromide (8.327 g) in EtOH (110 mL) and THF (60 mL) was added dropwise a solution of AgNO$_3$ (7.994 g) in H$_2$O (10 mL). The mixture was refluxed for 1 h and filtered while hot. The filter cake was washed with hot THF (2×30 mL). The combined filtrate was concentrated in vacuo to give crude 1-(3-Iodophenyl)-3-isoquinoline-carboxaldehyde as an dark yellow oil (11.62 g, containing H$_2$O). This oil was used without further purification. To a solution of crude aldehyde (11.62 g) in absolute EtOH (80 mL)was slowly added a solution of AgNO$_3$ (7.28 g) in H$_2$O (10 mL). To this stirred solution was added dropwise a solution of NaOH (5.80 g) in H$_2$O (100 mL). The resulting black slurry was stirred at room temperature for 2 h. Then the mixture was filtered through a small Celite column. The filter cake was washed with ether. The ether was evaporated and the aqueous solution was made slightly acidic with concentrated HCl. The precipitate was collected by filtration, then washed with H$_2$O. It was recrystallized from CH$_3$CN, thereby affording 1-(3-iodophenyl)-3-isoquinolinecarboxylic acid as a yellow crystalline (2.22 g, 36%). mp 145–146° C. $^1$H NMR (DMSO-d$_6$) d 7.37 (t, J=6.0 Hz, 1 H, aromatic), 7.65–7.71(m, 2 H, aromatic), 7.80 (t, J=4.8 Hz, 1 H, aromatic), 7.91 (d, J=6.6 Hz, 1 H, aromatic), 7.95 (d, J=6.3 Hz, 1 H, aromatic), 8.01 (s, 1 H, aromatic), 8.14 (d, J=6.0 Hz, 1 H, aromatic), 8.44 (s, 1 H, aromatic). HRMS Calcd for C$_{16}$H$_{10}$INO$_2$: 374.9756. Found: 374.9741.

Example 9

1-(4-iodophenyl)-3-isoquinolinecarboxylic Acid (7c)

A mixture of 1-(4-iodophenyl)-3-methylisoquinoline (2.59 g, 7.50 mmol), N-bromosuccinimide (NBS) (2.71 g, 15.22 mmol), and benzoyl peroxide (BPO) (0.14 g) in CCl$_4$ (80 mL) was heated to reflux while being illuminated by a flood lamp for 5 h. The reaction mixture was cooled to room temperature and filtered. The filtrate was washed with saturated NaHCO$_3$ aqueous solution (20 mL), dried (Na$_2$ SO$_4$), then filtered. The filtrate was concentrated in vacuo, thereby affording crude 1-(4-iodophenyl)-3-dibromomethylisoquinoline (6.10 g) as a yellow oil. It was used directly in next step without any purifications. To a refluxing solution of crude dibromide (6.10 g) in EtOH (80 mL) and THF (40 mL) was added dropwise a solution of AgNO$_3$3 (3.70 g) in H$_2$O (3 mL). The mixture was refluxed for 1 h and filtered while hot. The filter cake was washed with hot THF (2×20 mL). The combined filtrate was concentrated in vacuo to give crude 1 -(4-Iodophenyl)-3-isoquinoline-carboxaldehyde as an dark yellow oil (5.55 g). This oil was used without further purification. To a solution of crude aldehyde (5.55 g) in absolute EtOH (100 mL) was slowly added a solution of AgNO$_3$ (5.01 g) in H$_2$O (9 mL). To this stirred solution was added dropwise a solution of NaOH (4.91 g) in H$_2$O (70 mL). The resulting black slurry was stirred at room temperature for 2 h. Then the mixture was filtered through a small Celite column. The filter cake was washed with ether. The ether was evaporated and the aqueous solution was made slightly acidic with concentrated HCl. The precipitate was collected by filtration, then washed with H$_2$ O. It was recrystallized from CH$_3$CN, thereby affording the title compound as a pale yellow solid (1.005 g, 37%). mp 243.4–244.90° C. $^1$H NMR (DMSO-d$_6$) d 7.44 (d, J=8.1 Hz, 1 H, aromatic), 7.59 (d, J=8.1 Hz, 1 H, aromatic), 7.68–7.78 (m, 2 H, aromatic), 7.84 (t, J=7.8 Hz, 1 H, aromatic), 7.90 (d, J 8.4 Hz, 1 H, aromatic), 7.97 (d, J=8.4 Hz, 1 H, aromatic), 8.20 (d, J=8.1 Hz, 1 H, aromatic), 8.56 (s, 1 H, aromatic). HRMS Calcd for C$_{16}$H$_{10}$INO$_2$: 374.9756. Found: 374.9761.

Example 10

1-(2-iodophenyl)-N-methyl-3-isoquinoline carboxamide (8a)

To a mixture of 1-(2-iodophenyl)-3-isoquinolinecarboxylic acid (0.1868 g, 0.5 mmol), benzotriazol-1-yloxy-tris (demethylamino) phosphonium hexafluorophosphate (BOP) (0.2219 g, 0.5 mmol), Methylamine hydrochloride (0.1019 g, 1.5 mmol) in DMF (8 mL) was added Et$_3$N (0.42 mL, 4.5 mmol). The resulting mixture was stirred under Ar at room temperature for 7 h and quenched by adding H$_2$O (10 mL). The mixture was extracted with CH$_2$Cl$_2$ (3×15 mL). The combined organic layers were dried (MgSO$_4$), filtered. The filtrate was concentrated in vacuo. The residue was purified on column (SiO$_2$, 50% ethyl acetate/hexane, 0.1% Et$_3$N), thereby giving a white foam (0.1237 g, 65%). mp: 167–168° C. $^1$H NMR (CDCl$_3$) d 3.03, 3.05 (two s, 3 H, N-methyl), 7.25 (t, J=10.5 Hz, 1 H, aromatic), 7.39 (d, J=7.5 Hz, 1 H), 7.48–7.68 (m, 3 H, aromatic), 7.75 (t, J=9 Hz, 1 H, aromatic), 8.02–8.06 (m, 2 H, aromatic), 8.18 (br s, 1 H, NH), 8.65 (s, aromatic). $^{13}$C NMR (CDCl$_3$) d 26.13 (q, N-methyl), 97.79 (s, C—I), 120.02 (d, aromatic), 127.29 (d, aromatic), 127.75 (d, aromatic), 127.98 (d, aromatic), 128.53 (d, aromatic), 128.76 (d, aromatic), 130 13 (d, aromatic), 130.31 (d, aromatic), 130.81 (d, aromatic), 136.81 (s, aromatic), 139.42 (d, aromatic), 142.59 (s, aromatic), 143.30 (s, aromatic), 160.79 (s, aromatic), 165.32 (s, —CO—). HRMS calcd. for C$_{17}$H$_{13}$IN3IN$_2$O: 388.0073. Found: 388.0070.

Example 11

1-(3-iodophenyl)-N-methyl-3-isoquinoline carboxamide (8b)

To a mixture of 1-(3-iodophenyl)-3-isoquinolinecarboxylic acid (0.1186 g, 0.32 mmol), BOP (0.1402 g, 0.32 mmol), Methylamine hydrochloride (0.083 g, 1.23 mmol) in DMF (10 mL) was added Et$_3$N (0.17 mL, 1.22 mmol). The resulting mixture was stirred under Ar at room temperature for 7 h and quenched by adding H$_2$O (10 mL). The mixture was extracted with CH$_2$Cl$_2$ (3×15 mL). The combined organic layers were dried (MgSO$_4$), filtered. The filtrate was concentrated in vacuo. The residue was purified on column (SiO2, 35% ethyl acetate/hexane, 0.1% Et$_3$N), thereby giving a white solid (59.2 mg, 48%). mp 172.1–173.6° C. $^1$H NMR (CDCl$_3$) d 3.03, 3.04 (two s, 3 H, N-methyl), 7.24 (t, J=8.7 Hz, 1 H, aromatic), 7.55–7.65 (m, 2 H, aromatic), 7.71 (t, J=8.1 Hz, 1 H, aromatic), 7.82 (d, J=8.7 Hz, 1 H, aromatic), 7.95–8.05 (m, 3 H, aromatic), 8.19 (br s, 1 H, CONH), 8.57 (s, 1 H, aromatic). $^{13}$C NMR (CDCl$_3$) d 26.16 (q, N-methyl), 94.24 (s, C—I), 119.86 (d, aromatic), 127.15 (d, aromatic), 128.70 (d, aromatic), 128.96 (d, aromatic), 129.13 (d, aromatic), 129.91 (d, aromatic), 130.77 (d, aromatic), 137.14 (s, aromatic), 137.85 (d, aromatic), 138.57 (d, aromatic), 140.99 (s, aromatic), 142.67 (s, aromatic), 157.62 (s, aromatic), 165.25 (s, CO). HRMS calcd. for C$_{17}$H$_{13}$IN$_2$O: 388.0073. Found: 388.0071.

Example 12

1-(4-iodophenyl)-N-methyl-3-isoquinoline carboxamide (8c)

A mixture of 1-(4-iodophenyl)-3-isoquinolinecarboxylic acid (0.2073 g, 0.55 mmol), BOP (0.2447 g, 0.55 mmol), Methylamine hydrochloride (0.096 g, 1.42 mmol), and Et$_3$N (0.25 mL, 1.80 mmol) in DMF (8 mL) was stirred under Ar at room temperature. After stirring for 1 h , additional Et$_3$N (0.2 ml,) was added in one portion. The mixture was stirred under Ar for 7 h, then quenched by adding H$_2$O (8 mL). The resulting mixture was extracted with CH$_2$Cl$_2$ (3×20 mL). The combined organic layers were dried (Na$_2$SO$_4$), then filtered. The filtrate was concentrated in vacuo. The residue was purified on column chromatography (SiO$_2$, 35% ethyl acetate in hexane, 0.1% Et$_3$N), thereby affording the title compound as a white solid (0.1724, 81%). mp 163–164 ° C. $^1$H NMR (CDCl$_3$) d 3.07, 3.09 (two s, total 3 H, N-methyl), 7.46 (d, J=8.4 Hz, 2 H, aromatic), 7.64 (t, J=7.2 Hz, 1 H, aromatic), 7.77 (t, J=6.9 Hz, 1 H, aromatic), 7.92 (d, J=8.4 Hz, 2 H, aromatic), 8.07 (t, J=7.8 Hz, 2 H, aromatic), 8.24 (br s, 1 H, NH), 8.02 (s, 1 H, aromatic). $^{13}$C NMR (CDC$_{l3}$) d 26.05 (q,N-methyl), 95.14 (s, C—I), 119.54 (d, aromatic), 127.02 (d, aromatic), 128.58 (d, aromatic), 128.75 (di aromatic), 130.60 (d, aromatic), 131.43 (d, aromatic), 131.56 (aromatic), 137.02 (s, aromatic), 137.40 (d, aromatic), 138.28 (s, aromatic), 142.58 (s, aromatic), 158.09 (s, aromatic), 165.12 (s, CO). HRMS calcd. for C$_{17}$H$_{13}$IN$_2$O: 388.0073. Found: 388.0077.

Example 13

1-(2-iodophenyl)-N-methyl-N-(3-fluoropropyl)-3-isoquinolinecarboxamide (9a)

To a solution of 1-(2-iodophenyl)-N-methyl-3-isoquinolinecarboxamide (22 mg, 0.06 mmol) in DMF (2 mL) was added 60% NaH (12 mg, 0.30 mmol) in one portion. The mixture was stirred under Ar at room temperature for 40 min. Then, 3-fluoropropyl bromide (22 ul, 0.30 mmol) was added. After stirring under Ar at room temperature for 24 h, the mixture was quenched by adding H$_2$O (7 mL). The mixture was extracted with CH$_2$Cl$_2$ (3×15 mL). The combined organic layers were dried (MgSO$_4$), filtered. The filtrate was concentrated in vacuo. The residue was chromatographed (SiO$_2$, 30% ethyl acetate/hexane, 0.035% Et$_3$N), thereby affording a semisolid (6 mg, 23%), and starting material (17.7 mg). $^1$H NMR (CDCl$_3$) d 1.96–2.22 (m, 2 H, CH$_2$), 3.16, 3.20 (two s, total 3 H, N-methyl), 3.59–3.85 (m, 2 H, N—CH$_2$), 4.47 (qt, J=79.8, 47.1, 6 Hz, 2 H, CH$_2$F), 7.21 (dt, J=7.5, 0.9 Hz, 1 H, aromatic), 7.36 (dd, J=7.5, 1.5 Hz, 1 H, aromatic), 7.51 (t, J=7.2 Hz, 1 H, aromatic), 7.56 (d, J=3.9 Hz, 2 H, aromatic), 7.69–7.81 (m, 1 H, aromatic), 7.99 (t, J=7.8 Hz, 1 H, aromatic), 8.11, 8.18 (two s, total 1 H, aromatic). HRMS calcd. for C$_{20}$H$_{18}$FIN$_2$O: 448.0448. Found: 448.0456.

Example 14

1-(2-iodophenyl)-N-methyl-N-(3-[$^{18}$F] fluoropropyl)-3-isoquinolinecarboxamide [$^{18}$F] (9a)

Approximately 280 μl of 95% enriched $^{18}$O water containing 182 mCi NCA[$^{18}$F] fluoride was added to a Wheaton 5 mL micro-vial containing 1 ml of a solution containing 10 mg K-222 ("Kyrptofix"), 1 mg potassium carbonate, 0.05 ml water and 0.95 mL MeCN. The solution was heated at 116° C. for 3.5 minutes after which three additional portions of 2 mL MeCN was added and evaporated to dry the fluoride. The vial was cooled to room temperature and 5.5 mg of 14 dissolved in 1.0 ml MeCN was added. The solution was heated to 85° C. for 10 minutes, cooled to room temperature, and passed through a Waters classic SiO$_2$ sep-pak into a 10 mL maxi-vial attached to a 50 ml round bottomed flask. The sep-pak was rinsed with 5 ml of Et$_2$O, which was added to the maxi-vial, bringing the total volume to 5 mL. The resulting ethereal solution was evaporated in vacuo to afford 46.9 mCi (80 mCi EOB) [$^{18}$F] (9a). The resulting residue was diluted to 1.0 ml with 70% MeOH/H$_2$O, 0.1% Et$_3$N and loaded onto a reverse phase prep column, (Waters, 25 mm×100 mm, flow rate 5 ml/min) The fraction eluting at 16 minutes contained 13 mCi (29 mCi, 16%, based on E.O.B) of the desired product, in a synthesis time of 120 min. Radio-TLC (SiO$_2$ 2% methanol/methylene chloride), Rf=0.7) and radio-HPLC analysis (Waters, 8 mm×200 mm Novapak, 70% MeOH/H$_2$O, 0.1% Et$_3$N, flow rate lml/min, rt=3.6 min) showed these fractions to have a radiochemical purity of greater than 99% and to have a specific activity of at least 1.3×10$^3$Ci/mmol. The fractions containing the greatest radioactivity were concentrated in vacuo, dissolved in sterile saline w/10% EtOH, and filtered through a Gelman 0.2 micron filter for in vivo studies.

Example 15

1-(2-[$^{123}$I]iodophenyl)-N-methyl-N-(3-fluoropropyl)-3-isoquinolinecarboxamide [$^8$F] (9a)

The tributyltin precursor 15 (0.45 mg, 0.68 μmole) was treated with 3.4 mCi (500 μL) sodium [$^{123}$I]iodide (NCA), 5% HOA/MeOH (300 μL) followed by addition of 1% NCS in MeOH (50 μL, 2.5 μmole). The reaction mixture was quenched after 15 min with 40 μL of aqueous sodium bisulfite solution (0.72 mg/mL). The resulting solution was diluted with ethyl acetate (1 mL), dried with $Na_2SO_4$, concentrated in vacuo and loaded on 2 preconditioned $C_{18}$ Sep-Pak and then rinsed with 10 mL of water. Elution with 75% MeOH, 0.1% $Et_3N$ in water The fractions (2–5, 1 mL each) contained 1.45 mCi (2 mCi, 60%, based on E.O.B) of the desired product, in a synthesis time of 120 min. Radio-TLC ($SiO_2$ 2% methanol/methylene chloride), Rf=0.7) and radio-HPLC analysis (Waters, 8 mm×200 mm Novapak, 70% MeOH/$H_2O$, 0.1% $Et_3N$, flow rate 1 ml/min, rt=3.6 min) showed these fractions to have a radiochemical purity of greater than 97% and to have a specific activity of at least $1.0 \times 10^3$ Ci/mmol. The fractions containing the greatest radioactivity were concentrated in vacuo, dissolved in sterile saline w/10% EtOH, and filtered through a Gelman 0.2 micron filter for in vivo studies.

Example 16

1-(3-iodophenyl)-N-methyl-N-(3-fluoropropyl)-3-isoquinolinecarboxamide (9b)

To a solution of 1-(3-iodophenyl)-N-methyl-3-isoquinolinecarboxamide (22 mg, 0.06 mmol) in DMF (4.6 mL) was added 60% NaH (16 mg, 0.39 mmol) in one portion. The mixture was stirred under Ar at room temperature for 15 min. Then, 3-fluoropropyl bromide (29 μl, 0.39 mmol) was added. After stirring at room temperature for 20 h, the mixture was quenched by adding $H_2O$ (5 mL). The mixture was extracted with $CH_2Cl_2$ (3×15 mL). The combined organic layers were dried (MgSO4), filtered. The filtrate was concentrated in vacuo. The residue was chromatographed (SiO2, 30% ethyl acetate/hexane, 0.035% $Et_3N$), thereby affording a semisolid (4.4 mg, 37%). $^1$H NMR (CDCl$_3$) d 2.04–2.24 (m, 2 H, $CH_2$), 3.16, 3.18 (two s, total 3 H, N-methyl), 3.60–3.75 (m, 2 H, N—$CH_2$), 4.25–4.70 (qt, J=67.8, 47.1, 5.7 Hz, 2 H, $CH_2F$), 7.20–7.30 (m, 1 H, aromatic), 7.55–7.65 (m, 2 H, aromatic), 7.73 (t, J=7.2 Hz, 1 H, aromatic), 7.83 (d, J=7.8 Hz, 1 H, aromatic), 7.94 (d, J=8.4 Hz, 1 H, aromatic), 7.98–8.09 (m, 2 H, aromatic), 8.12 (s, 1 H, aromatic). HRMS calcd. for $C_{20}H_{18}FIN_2O$: 448.0448. Found: 448.0461

Example 17

1-(4-iodophenyl)-N-methyl-N-(3-fluoropropyl)-3-isoquinolinecarboxamide (9c)

To a solution of 1-(4-iodophenyl)-N-methyl-3-isoquinolinecarboxamide (25 mg, 0.06 mmol) in DMF (4 mL) was added 60% NaH (10 mg, 0.25 mmol) in one portion. The mixture was stirred under Ar at room temperature for 30 min. Then, 3-fluoropropyl bromide (20 μl, 0.27 mmol) was added. After stirring at room temperature for overnight, the mixture was quenched by adding $H_2O$ (5 mL). The mixture was extracted with $CH_2Cl_2$ (3×15 mL). The combined organic layers were dried (MgSO$_4$), filtered. The filtrate was concentrated in vacuo. The residue was chromatographed ($SiO_2$, 30% ethyl acetate/hexane, 0.035% $Et_3N$), thereby affording a semisolid (11 mg, 40%). $^1$H NMR (CDCl$_3$) d 2.01–2.22 (m, 2 H, $CH_2$), 3.15, 3.17 (two s, total 3 H, N-methyl), 3.60–3.76 (m, 2 H, N—$CH_2$), 4.22–4.76 (qt, J=77.7, 47.1, 5.7 Hz, 2 H, $CH_2F$), 7.36–7.47 (m, 1 H, aromatic), 7.50–7.81 (m, 4 H, aromatic), 7.82–7.99 (m, 2 H, aromatic), 7.83–8.16 (m, 2 H, aromatic). HRMS calcd. for $C_{20}H_{18}FIN_2O$: 448.0448. Found: 448.0435.

Example 18

1-(2-iodophenyl)-N-methyl-N-(2-fluoroethyl)-3-isoquinolinecarboxamide (9d)

To a solution of 1-(2-iodophenyl)-N-methyl-3-isoquinolinecarboxamide (0.1042 g, 0.27 mmol) in DMF (6 mL) was added 60% NaH (43 mg, 1.08 mmol) in one portion. The mixture was stirred under Ar at room temperature for 30 min before 2-fluoroethylbromide (161 μl, 2.16 mmol) was added in one portion. The mixture was stirred at room temperature under Ar for 20 h, then quenched by adding $H_2O$ (5 mL). The mixture was extracted with $CH_2Cl_2$ (3×15 mL). The combined organic layers were dried (MgSO$_4$), and filtered. The filtrate was concentrated in vacuo. The residue was purified on flash column chromatography ($SiO_2$, 30% ethyl acetate/hexane, 0.035% $Et_3N$). A white solid (48 mg, 41%) was obtained. mp 141.9–143.2° C. $^1$H NMR (CDCl$_3$) d 3.22, 3.27 (two s, 3 H, N-methyl), 3.67–4.15 (m, 2 H, N—$CH_2$), 4.42–4.92 (m, 2 H, $CH_2F$), 7.15–7.25 (m, 1 H, aromatic), 7.27–7.37 (m, 1 H, aromatic), 7.45–7.64 (m, 3 H, aromatic), 7.67–7.77 (m, 1 H, aromatic), 7.97 (t, J=7.5 Hz, 2 H, aromatic), 8.11, 8.21 (two s, total 1 H, aromatic). Anal. Calcd for $Cl_{19}H_{16}FIN_2O$: C, 52.55; H, 3.71; N, 6.45. Found: C, 52.64; H, 3.78; N, 6.38.

Example 19

1-(2-iodophenyl)-N-methyl-N-(3-triphenyl methoxypropyl)-3-isoquinoline-carboxamide (12)

A mixture of 1-(2-iodophenyl)-N-methyl-3-isoquinolinecarboxamide (71.5 mg, 0.18 mmol) and NaH (60%, 31.5 mg, 0.79 mmol) in DMF (8 mL) was stirred at room temperature for 30 min. To this mixture was added dropwise a solution of 3-triphenylmethoxypropyl bromide (566 mg, 1.48 mmol) in DMF (2 mL). The resulting mixture was stirred under Ar at room temperature for overnight and then quenched by adding $H_2O$ (5 mL). The mixture was extracted with $CH_2Cl_2$ (3×20 mL). The combined organic layers were dried (MgSO$_4$), filtered. The filtrate was concentrated in vacuo. The residue was purified on column chromatography (silical gel, 50% ethyl acetate/hexane, 0.1% $Et_3N$), thereby affording a white foam (0.1245 g, 98%). mp 70–71° C. $^1$H NMR (CDCl$_3$) d 1.82–1.98 (m, 2, $CH_2$), 2.95–3.05 (m, 2 H, $CH_2OH$), 3.21 (m, 1 H, OH), 3.52–3.88 (m, 2 H, N—$CH_2$), 7.10–7.58 (m, 20 H, aromatic), 7.62–7.78 (m, 1 H, aromatic), 7.92 (d, J=7.8 Hz, 2 H, aromatic), 8.01 (d, J=6 Hz, 1 H, aromatic). HRFABMS Cacld. for $C_{36}H_{33}ILiN_2O_2$: 695.1747 (M+Li)+. Found: 695.1763.

Example 20

1-(2-iodophenyl)-N-methyl-N-(3-hydroxypropyl)-3-isoquinolinecarboxamide (13)

To a solution of 1-(2-iodophenyl)-N-methyl-N-(3-triphenylmethoxy-propyl)-3-isoquinolinecarboxamide (107 mg, 0.16 mmol) in $CH_2Cl_2$ (10 mL) was added dropwise TFA (1 mL). The mixture was stirred at room temperature for 40 min. Then it was transferred into a separatory funnel and washed with saturated NaHCO$_3$ solution (2×10 mL), water (20 mL), and brine (20 mL), then dried (MgSO$_4$), and filtered. After removing the solvent in vacuo, the residue was purified on column (silica gel, 2% MeOH/CH$_2$Cl$_2$, 0.1% Et$_3$N), thereby affording starting material (5.2 mg) and the titled compound (51.2 mg, 73%). mp 51–52° C. $^1$H NMR (CDCl$_3$) d 1.78–1.95 (m, 2 H, CH$_2$), 3.12, 3.19 (two s, total 3 H, N—Me), 3.52–3.74 (m, 3 H), 3.82–4.32 (m, 2 H), 7.19–7.31 (m, 1 H, aromatic), 7.35–7.42 (m, 1 H, aromatic), 7.48–7.63 (m, 3 H, aromatic), 7.72–7.81 (m, 2 H, aromatic), 8.17, 8.26 (two s, total 1 H, aromatic). HRMS Cacld. for C$_{20}$H$_{19}$IN$_2$O: 446.0491. Found: 446.0501.

Example 21

1-(2-iodophenyl)-N-methyl-N-(3-mesylpropyl)-3-isoquinolinecarboxamide (14)

To a solution of 1-(2-iodophenyl)-N-methyl-N-(3-hydroxypropyl)-3-isoquinolinecarbo-xamide (20 mg, 0.045 mmol), DMAP (5.5 mg, 0.045 mmol), and Et$_3$N (0.02 mL, 0.14 mmol) in CH$_2$Cl$_2$ (2 mL) at 0° C. was added dropwise MsCl (0.006 mL, 0.77 mmol). The resulting mixture was stirred at 0° C. and monitored by TLC. After stirring at 0° C. for 4 h, TLC showed that no starting material left. Then, it was transferred into separatory funnel and washed with H$_2$O (15 mL) The organic layer was dried (MgSO$_4$), and filtered. The filtrate was concentrated in vacuo. The residue was purified on column (silica gel, 2% MeOH/CH$_2$Cl$_2$, 0.1% Et$_3$N), thereby affording an oil (16 mg, 68%). $^1$H NMR (CDCl$_3$) d 2.12–2.22 (m, 2 H, CH$_2$), 2.77, 3.06 (two s, total 3 H, —SO$_2$Me), 3.17, 3.20 (two s, total 3 H, N—Me), 3.62–3.82 (m, 2 H, N—CH$_2$), 4.15 (t, J=6.0 Hz, 1 H, CH$_2$O), 4.39 (t, J=6.0 Hz, 1 H, CH$_2$O), 7.19–7.27 (m, 1 H, aromatic), 7.39–7.41 (m, 1 H, aromatic), 7.48–7.64 (m, 3 H, aromatic), 7.73–7.79 (m, 1 H, aromatic), 7.96–8.05 (m, 2 H, aromatic), 8.12, 8.24 (two s, total 1 H, aromatic). HRFABMS Cacld. for C$_{21}$H$_{21}$ILiN$_2$O$_4$S: 531.0427 (M+Li)+. Found: 531.0443.

Example 22

1-(2-trimethylstannylphenyl)-N-methyl-N-(3-fluoropropyl)-3-isoquinoline-carboxamide (15)

To a solution of 1-(2-iodophenyl)-N-methyl-N-(3-fluoropropyl)-3-isoquinolinecarboxamide (49,8 mg, 0.11 mmmol) in toluene (12 mL) under Ar was added Pd(PPh$_3$)4 (8.8 mg, 0.0076 mmol), Pd(OAc)2 (9.8 mg, 0.044 mmol), and (Me$_3$Sn)2 (0.1497 g, 0.46 mmol). The resulting mixture was refluxed under Ar for 20 h. Then it was cooled to room temperature. The mixture was applied on column chromatography (silica gel, 30% ethyl acetate/hexane, 0.035% Et$_3$N), thereby affording the title compound (22 mg, 41%) as a light brown oil. $^1$H NMR (CDCl$_3$) d −0.20, −0.17 (two s, total 9 H, SnMe$_3$), 1.85–2.22 (m, 2 H, CH$_2$), 3.08, 3.14 (two s, total 3 H, N-methyl), 3.52–3.76 (m, 2 H, CH$_2$), 4.39 (qt, J=118.8, 47.4, 5.7 Hz, 2 H. CH$_2$F), 7.41–7.62 (m, 4 H, aromatic), 7.66–7.78 (m, 2 H, aromatic), 7.88–8.18 (m, 3 H, aromatic). HRMS Calcd for C$_{22}$H$_{24}$FIN$_2$OSn (M−CH$_3$)+: 471.0895. Found: 471.0908.

Example 23

1-(2-tributylstannylphenyl)-N-methyl-3-isoquinoline-carboxamide (16)

A mixture of 1-(2-iodophenyl)-N-methyl-3-isoquinoline-carboxamide (100 mg, 0.26 mmol), Pd(OAc)2 (8.8 mg, 0.039 mmol), Pd(PPh$_3$)4 (15.3 mg, 0.013 mmol), and bis (tributylditin) (0.94 mL, 1.86 mmol) in toluene (7 mL) was refluxed under Ar for 20 h. After non-aqueous work-up and purification on column chromatography (silical gel, 10–15% ethyl acetate/hexane, 0.1% Et$_3$N), thereby affording a white solid. mp 97–98° C. $^1$H NMR (CDCl$_3$) d 0.35–0.82 (m, 6 H, SnCH$_2$), 0.709 (t, J=7.2 Hz, 9 H, CH$_3$), 1.01–1.32 (m, 12 H, CH$_2$CH$_2$), 3.05 (d, J=5.1 Hz, 3 H, N-methyl), 7.49–7.51 (m, 3 H, aromatic), 7.57 (t, J=7.2 Hz, 1 H, aromatic), 7.68–7.79 (m, 2 H, aromatic), 7.86 (d, J=8.4 Hz, 1 H, aromatic), 8.05 (d, J=8.1 Hz, 1 H, aromatic), 8.21 (br s, 1 H, NH), 8.65 (s, 1 H, aromatic). HRFABMS Calcd. for C$_{29}$H$_{41}$N$_2$O$_{12}$OSn: 553.2230. Found: 553.2241.

Example 24

1-(2-tributylstannylphenyl)-N-methyl-N-(3-fluoropropyl)-3-isoquinoline-carboxamide (17)

To a solution of 1-(2-tributylstannylphenyl)-N-methyl-3-isoquinoline-carboxamide (105 mg, 0.19 mmol) in DMF (5 mL) was added 60% NaH (65 mg, 1.61 mmol) in one portion. The mixture was stirred under Ar at room temperature for 40 min. Then, 3-fluoropropyl bromide (124 μl, 1.67 mmol) was added. After stirring under Ar at room temperature for 24 h, the mixture was quenched by adding H$_2$O (9 mL). The mixture was extracted with CH$_2$Cl$_2$ (3×15 mL). The combined organic layers were dried (MgSO$_4$), filtered. The filtrate was concentrated in vacuo. The residue was chromatographed (SiO$_2$, 5–10% ethyl acetate/hexane, 0.1% Et$_3$N), thereby affording an oil (29.3 mg, 25%), and starting material (62.5 mg). $^1$H NMR (CDCl$_3$) d 0.32–0.68 (m, 6 H, SnCH$_2$), 0.70 (t, J=7.2 Hz, 9 H, CH$_3$), 0.95–1.32 (m, 12 H, CH$_2$CH$_2$), 2.15–2.28 (m, 2 H, CH$_2$), 3.13 (d, J=11.1 Hz, 3 H, N-methyl), 3.58–3.85 (m, 2 H, N—CH$_2$), 4.48 (qt, J=123.9, 47.4, 5.7 Hz, 2 H, CH$_2$F), 7.42–7.62 (m, 4 H, aromatic), 7.65–7.80 (m, 2 H, aromatic), 7.91–8.15 (m, 3 H, aromatic). HRFABMS Calcd. for C$_{32}$H$_{46}$FN$_2$O$_{12}$OSn: 613.2599. Found: 613.2619.

Example 25

4-tosylbutan-2-ol (19)

To a mixture of 1,3-butandiol (1.0 g, 11.1 mmol), Et$_3$3N (1.6 mL, 11.5 mmol) in CH$_2$Cl$_2$ (10 mL) at 0° C. was added dropwise a solution of TsCl(2.12 g, 11.1 mmol) in CH$_2$Cl$_3$ (5 mL). The resulting mixture was stirred at 0° C. and warmed gradually to room temperature, then kept at room temperature for overnight. It was transferred into a separatory funnel and washed with H$_2$O (3×20 mL). The organic layer was dried (MgSO$_4$), filtered. The filtrate was concentrated in vacuo. The residue was purified on column chromatography (silical gel, 30% ethyl acetate/hexane), thereby affording a colorless oil (1.3 g, 48%). $^1$H NMR (CDCl$_3$) d 1.07 (d, J=6.0 Hz, 3 H, CH$_3$), 1.52–1.76 (m, 2 H, CH$_2$), 2.33 (s, 3 H, CH$_3$), 3.84 (br s, 1 H, OH), 4.08–4.20 (m, 2 H, CH$_2$), 7.25 (d, J=8.4 Hz, 2 H, aromatic), 7.77 (d, J=8.1 Hz, 2 H, 5 aromatic). $^{13}$C NMR (CDCl$_3$) d 21.60 (q, CH$_3$), 23.58 (q, CH$_3$), 37.86 (t, CH$_2$), 64.10 (d, CH), 67.79 (t, CH$_2$OTs), 127.85 (d, aromatic) 129.84 (d, aromatic), 144.78 (s, aromatic), 152.23 (s, aromatic).

Example 26

4-fluorobutan-2-ol (20)

A mixture of 4-tosylbutan-2-ol (1.11 g, 4.5 mmol) and Bu4N$^+$F$^-$ (1M , 4.8 mL, 4.8 mmol) in THF (20 mL) was refluxed for 18 h. The solvent was removed bu distillation. The residue was distilled by Kugelrohr, thereby giving an oil (0.32 g, 77%). $^1$H NMR (CDCl$_3$) d 1.18 (d, J=6.0 Hz, 3 H, CH$_3$), 1.62–1.90 (m, 2 H, CH$_2$), 2.35 (br s, 1 H, OH), 3.89–4.03 (m, 1 H, CH), 4.38–4.71 (m, 2 H, CH$_2$F). $^{13}$C NMR (CDCl$_3$) d 23.55 (q, CH$_3$), 39.26 (t, J=18.75 Hz, CH$_2$), 64.71 (d, J=4.95 Hz, CH), 81.69 (t, J=161.25 Hz, CH$_2$F).

Example 27

1-fluoro-3-trifluoacetoxybutane (21)

To a solution of 4-fluorobutan-2-ol (0.3139 g, 3.41 mmol) and Et$_3$N (0.71 mL, 5.1 mmol) in CH$_2$Cl$_2$ (9 mL) under Ar at 0° C. was added dropwise Tf$_2$O (0.86 mL, 5.1 mmol). The resulting mixture was stirred under Ar at 0° C. for 30 min. It was quenched by adding ice. After it was stirred for 10 min, it was transferred into a separatory funnel, and washed with cold H$_2$O (2×20 mL). The organic layer was dried (Na$_2$SO$_4$), filtered. The filtrate was concentrated in vacuo. A light brown oil (0.6444 g) was obtained. It was used directly in the next step without further purification. $^1$H NMR (CDCl$_3$) d 1.59 (d, J=4.8 Hz, 3 H, CH$_3$), 2.08–2.15 (m, 2 H, CH$_2$), 4.48–4.65 (m, 2 H, CH$_2$F), 5.18–5.30 (m, 1 H, CH). The compound was used directly in the next step without any further purification.

Example 28

N-methyl-4-fluoro-2-butylamine (22)

A mixture of 1-fluoro-3-trifluoacetoxybutane (0.2653 g, 1.18 mmol) and MeNH$_2$(2M solution in THF, 0.6 mL, 1.2 mmol) was heated at 60° C. for 4 h. The mixture was acidified to pH<2 by adding concentrated HCl. The solvent was removed in vacuo. The residue was dissolved in H$_2$O (5 mL) and extracted with ether (10 mL) The aqueous layer was basified to pH>10 by adding 30% NaOH solution, saturated with NaCl, then extracted with ether (4×10 mL). The ether layers were dried (K$_2$CO$_3$), filtered. The filtrate was concentrated in vacuo. $^1$H NMR (CDCl,) d 1.20 (d, J=4.8 Hz, 3 H, CH$_3$), 1.94–2.12 (m, 2 H, CH$_2$), 2.52 (s, 3 H, N—CH$_3$), 2.90–3.01 (m, 1 H, CH), 4.42–4.70 (m, 2 H, CH$_2$F), 4.78–4.83 (m, 1 H, NH). The compound was used directly in the next step without any further purification.

Example 29

1-(2-iodophenyl)-N-methyl-N-(4-fluor-2-butyl)-3-isoquinoline-carboxamide (23a)

To a solution of 1-(2-iodophenyl)-3-isoquinolinecarboxylic acid (54.4 mg, 0.15 mmol), BOP (65.4 mg, 0.15 mmol) in DMF (6 mL) under Ar was added a solution of N-methyl 3-fluoro-2-butylamine (333.3 mg, crude, excess) and Et$_3$N (21 μL, 0.15 mmol) in DMF (1.0 mL). The resulting mixture was stirred at ambient temperature for 7 h. Then it was quenched by adding H$_2$O (5 mL). The mixture was extracted with CH$_2$Cl$_2$ (3×20 mL). The organic layers were dried (Na$_2$SO$_4$), filtered. The filtrate was concentrated in vacuo. The residue was purified on column chromatography (silica gel, 30% ethyl acetate/hexane, 0.05% Et$_3$N) to give a yellow oil (36.2 mg). This oil was further purified on reverse phase HPLC (75% MeOH/H$_2$O, 0.1% Et$_3$N). Two major fractions were collected. The first fraction (Rt=13 min, 12 mg, 17%) was the title compound. mp 62–63.5° C. $^1$H NMR (CDCl$_3$) d 1.20–1.40 (m, 3 H, CH$_3$), 1.72–2.30 (m, 2 H, CH$_2$), 3.01, 3.02 (two s, total 3 H, N-methyl), 4.32–4.57 (m, 2 H, CH$_2$F), 4.60–4.71 (m, 0.5 H, CH), 4.92–5.02 (m, 0.5 H, CH), 7.21 (t, J=7.2 Hz, 1 H, aromatic), 7.32 (d, J=7.8 Hz, 1 H, aromatic), 7.46–7.64 (m, 3 H, aromatic), 7.72–7.83 (m, 1 H, aromatic), 7.95–8–19 (m, 3 H, aromatic). HRMS Cacld for C$_{21}$H$_{20}$FIN$_2$O: 462.0604. Found: 462.0598.

Example 30

1-(3-iodophenyl)-N-methyl-N-(4-fluor-2-butyl)-3-isoquinoline-carboxamide (23b)

To a solution of 1-(3-iodophenyl)-3-isoquinolinecarboxylic acid (52.2 mg, 0.14 mmol), BOP (64.2 mg, 0.15 mmol) in DMF (6 mL) under Ar was added a solution of N-methyl 3-fluoro-2-butylamine (420 mg, crude, excess) and Et$_3$N (20 μL, 0.14 mmol) in DMF (1.0 mL). The resulting mixture was stirred at ambient temperature for 7 h. Then it was quenched by adding H$_2$O (5 mL). The mixture was extracted with CH$_2$Cl$_2$ (3×20 mL). The organic layers were dried (Na$_2$SO$_4$), filtered. The filtrate was concentrated in vacuo. The residue was purified on column chromatography (silica gel, 30% ethyl acetate/hexane, 0.05% Et$_3$N) to give a yellow oil (41.1 mg). This oil was further purified on reverse phase HPLC (75% MeOH/H$_2$O, 0.1% Et$_3$N). After reverse phase HPLC purification, a pale yellow solid (17 mg, 26%) was obtained. mp 50–51.5° C. $^1$H NMR (CDCl$_3$) d 1.24–1.41 (m, 3 H, CH$_3$), 1.75–2.21 (m, 2 H, CH$_2$), 2.98, 3.01 (two s, total 3 H, N-methyl), 4.29–4.40 (m, 1 H, CH$_2$F), 4.44–4.58 (m, 1 H, CH$_2$F), 4.63–4.74 (m, 0.5 H, CH), 4.96–5.06 (m, 0.5 H, CH), 7.27 (dt, J=9.6, 1.8 Hz, 1 H, aromatic), 7.58–7.64 (m, 2 H, aromatic), 7.74 (t, J=6.9 Hz, 1 H, aromatic), 7.85 (d, J=7.8 Hz, 1 H, aromatic), 7.95 (d, J=8.1 Hz, 1 H, aromatic), 8.01–8.12 (m, 3 H, aromatic). HRMS Cacld for C$_{21}$H$_{20}$FIN$_2$O: 462.0604. Found: 462.0607.

Example 31

1-(4-iodophenyl)-N-methyl-N-(4-fluor-2-butyl)-3-isoquinoline-carboxamide (23c)

To a solution of 1-(4-iodophenyl)-3-isoquinolinecarboxylic acid (31.5 mg, 0.084 mmol), BOP (46.6 mg, 0.11 mmol) in DMF (5.0 mL) under Ar was added a solution of N-methyl 3-fluoro-2-butylamine (200 mg, crude, excess) and Et$_3$N (20 μL, 0.14 mmol) in DMF (1.0 mL). The resulting mixture was stirred at ambient temperature for 7 h. Then it was quenched by adding H$_2$O (5 mL). The mixture was extracted with CH$_2$Cl$_2$ (4×15 mL). The organic layers were dried (Na$_2$SO$_4$), filtered. The filtrate was concentrated in vacuo. The residue was purified on column chromatography (silica gel, 30% ethyl acetate/hexane, 0.05% Et$_3$N) to give a yellow oil (15.2 mg). This oil was further purified on reverse phase HPLC (75% MeOH/H$_2$O, 0.1% Et$_3$N). After reverse phase HPLC purification, a white foam (10 mg, 26%) was obtained. mp 53–54° C. $^1$H NMR (CDCl$_3$) d 1.20–1.40 (m, 3 H, CH$_3$), 1.70–2.20 (m, 2 H, CH$_2$), 2.98, 3.01 (two S, total 3 H, N-methyl) 4.30–4.41 (m, 1 H, CH$_2$F), 4.42–4.56 (m, 1 H, CH$_2$F), 4.62–4.64 (m, 0.5 H, CH), 4.92–5.02 (m, 0.5 H, CH), 7.41–7.48 (m, 2 H, aromatic), 7.60 (t, J=8.1 Hz, 1 H, aromatic), 7.73 (t, J=7.2 Hz, 1 H, aromatic), 7.88 (d, J=8.4 Hz, 2 H, aromatic), 7.95 (d, J=8.1 Hz, 1 H, aromatic), 8.01–8.12 (m, 2 H, aromatic). HRMS Cacld for C$_{21}$H$_{20}$FIN$_2$O: 462.0604. Found: 462.0604.

We claim:
1. A compound of the formula:

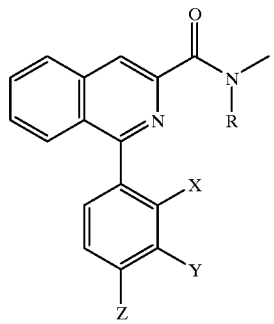

Wherein X, Y and Z, independently of one another, are selected from the group consisting of H, F, $^{18}$F, I, $^{123}$I, $^{124}$I, $^{125}$I, $^{131}$I, Br, $^{75}$Br, $^{76}$Br, $^{77}$Br, $^{82}$Br, $^{210}$At, $^{211}$ (R$_1$)W or (R$_2$)V; R is —(R$_1$)W, wherein W is selected from the group consisting of F, and $^{18}$F, and wherein R$_1$ is a linear or branched alkyl comprising from 1 to about 4 carbon atoms, R$_2$ is vinyl, wherein V is I, $^{123}$I, $^{124}$I, $^{125}$I or $^{131}$I; and at least one of X, Y or Z is not H.

2. The compound of claim 1 wherein R$_1$ is —(CH$_2$)$_3$—.
3. The compound of claim 2 wherein W is F.
4. The compound of claim 2 wherein W is $^{18}$F.
5. The compound of claim 1 wherein R$_1$ is —(CH$_2$)$_2$—.
6. The compound of claim 5 wherein W is F.
7. The compound of claim 5 wherein W is $^{18}$F.
8. The compound of claim 4 wherein X is selected from the group consisting of I, $^{123}$I, $^{124}$I, $^{125}$I, $^{131}$I, and wherein Y and Z are each H.
9. The compound of claim 4 wherein Y is selected from the group consisting of I, $^{123}$I, $^{124}$I, $^{125}$I, $^{131}$I, and wherein X and Z are each H.
10. The compound of claim 4 wherein Z is selected from the group consisting of I, $^{123}$I, $^{124}$I, $^{125}$I, $^{131}$I, and wherein Y and X are each H.
11. The compound of claim 1 wherein R is sec-butyl.
12. The compound of claim 11 wherein X is selected from the group consisting of I, $^{231}$I, $^{124}$I, $^{125}$I, $^{131}$I, and wherein Y and Z are each H.
13. The compound of claim 11 wherein Y is selected from the group consisting of I, $^{123}$I, $^{124}$I, $^{125}$I, $^{131}$I, and wherein X and Z are each H.
14. The compound of claim 11 wherein Z is selected from the group consisting of I, $^{123}$I, $^{124}$I, $^{125}$I, $^{131}$I, and wherein Y and X are each H.
15. The compound of claim 7 wherein X is selected from the group consisting of I, $^{123}$I, $^{124}$I, $^{125}$I, $^{131}$I, and wherein Y and Z are each H.
16. The compound of claim 3 wherein X is selected from the group consisting of I, $^{123}$I, $^{124}$I, $^{125}$I, $^{131}$I, and wherein Y and Z are each H.
17. The compound of claim 3 wherein Y is selected from the group consisting of I, $^{123}$I, $^{124}$I, $^{125}$I, $^{131}$I, and wherein X and Z are each H.
18. The compound of claim 3 wherein Z is selected from the group consisting of I, $^{123}$I, $^{124}$ I, $^{125}$I, $^{131}$I, and wherein Y and X are each H.

* * * * *

UNITED STATES PATENT AND TRADEMARK OFFICE
CERTIFICATE OF CORRECTION

PATENT NO. : 5,998,624

DATED : December 7, 1999

INVENTOR(S) : Goodman et al.

It is certified that error appears in the above-identified patent and that said Letters Patent is hereby corrected as shown below:

In Column 3, Line 2, delete "sara" and replace with --para--.

In Column 5, Line 5, delete "As".

In Column 11, the lower section of Scheme 6, delete "BO/Et$_3$N" and replace with --BOP/Et$_3$N--.

In Column 12, line 61, delete "55" and replace with --5%--.

In Column 17, line 15, delete "$C_{17}H_{13}IN3IN_2O$" and replace with --$C_{17}H_{13}IN_2O$--.

In Column 18, line 2, delete "di" and replace with --d,--.

UNITED STATES PATENT AND TRADEMARK OFFICE
CERTIFICATE OF CORRECTION

PATENT NO. : 5,998,624

DATED : December 7, 1999

INVENTOR(S) : Goodman et al.

It is certified that error appears in the above-identified patent and that said Letters Patent is hereby corrected as shown below:

In Column 19, line 4, delete "$[^{8}F]$" and replace with --$[^{18}F]$--.

In Column 20, line 52, delete "(m, 2, $CH_2$)," and replace with --(m, 2H, $CH_2$),--.

In Column 22, line 57, delete the last character in the line, "5".

In Column 24, line 3, delete "7.95-8-19" and replace with --7.95-8.19--.

In Column 24, line 60, delete "(two S," and replace with --(two s,--.

In the Claims:

In Column 25, line 20, delete "$^{211}$ ($R_1$W)" and replace with --$^{211}$At ($R_1$)W--.

In Column 26, line 12, delete "$^{231}I$" and replace with --$^{123}I$--.

Signed and Sealed this

Ninth Day of January, 2001

*Attest:*

Q. TODD DICKINSON

*Attesting Officer*     *Commissioner of Patents and Trademarks*